United States Patent [19]

Carr et al.

[11] Patent Number: 5,527,812
[45] Date of Patent: Jun. 18, 1996

[54] CYCLIC NITRONES

[75] Inventors: Albert A. Carr, Cincinnati; Craig E. Thomas, West Chester; Ronald C. Bernotas, Cincinnati; George Ku, West Chester, all of Ohio

[73] Assignee: Merrell Pharmaceuticals Inc., Cincinnati, Ohio

[21] Appl. No.: 458,318

[22] Filed: Jun. 2, 1995

Related U.S. Application Data

[62] Division of Ser. No. 352,470, Dec. 9, 1994, which is a division of Ser. No. 170,543, Dec. 20, 1993, Pat. No. 5,397,789, which is a division of Ser. No. 926,109, Aug. 5, 1992, Pat. No. 5,292,746, which is a continuation-in-part of Ser. No. 828,075, Jan. 30, 1992, abandoned, which is a continuation-in-part of Ser. No. 758,063, Sep. 12, 1991, abandoned.

[51] Int. Cl.⁶ .................................................. A61K 31/47
[52] U.S. Cl. .......................... 514/309; 514/213; 514/217; 514/278; 514/409; 514/416
[58] Field of Search ........................ 514/213, 217, 514/278, 309, 409, 416

[56] References Cited

U.S. PATENT DOCUMENTS

| | | | |
|---|---|---|---|
| 3,044,930 | 7/1962 | Goodhue | 514/311 |
| 3,795,715 | 3/1974 | Leimgruber et al. | 546/150 |
| 3,947,451 | 9/1975 | Jösson et al. | 260/287 |
| 4,117,144 | 9/1978 | Jösson et al. | 424/274 |
| 4,123,543 | 9/1978 | Jösson et al. | 424/274 |
| 5,025,032 | 6/1991 | Carney et al. | 514/400 |

FOREIGN PATENT DOCUMENTS 9105552  of 1991  WIPO.

OTHER PUBLICATIONS

Floyd, FASEB Journal, vol. 4, pp. 2587–2599 (1990).
Bolli et al., Free Rad. Res. Comm., vol. 9, Nos. 3–6, pp. 169–180, 1990.
Golubev, et al., Chemical Abstracts, vol. 77, No. 16, Abstract No. 114,165c, Oct. 16, 1972, pp. 428–429.
Oxidative damage to brain proteins, loss of glutamine synthetase activity, and production of free radicals during ischemia/reperfusion–induced injury to gerbil brain, Proc. Natl. Acad. Sci. USA vol. 87, pp. 5144–5147 Jul. 1990, Neurobiology.
Protection from cerebral ischemic injury in gerbils with the spin trap agent N–tert–butyl–a–phenylnitrone (PBN) Neuroscience Letters, 116 (1990) 315–319.
Seeger, et al., "Chem. Ber.", vol. 103, 1970, pp. 1674–1691.
Thomae, "Chemical Abstracts," vol. 74, 1971, col. 141572c.
Kobor, "Chemical Abstracts," vol. 77, 1972, col. 151841r.
Jonsson, et al., "Chemical Abstracts," vol. 78, 1973, col. 159460g.
Patent Abstracts of Japan vol. 12, No. 283 (C–518)(3130) 3 Aug. 1988 & JP–A–63 063 851 (Univ. Osaka) 22 Mar. 1988.
Interleukin–1 and Interleukin–1 Antagonism, Blood, vol. 77, No. 8 (Apr. 15), 1991: pp. 1627–1652, Charles A. Dinarello.
An Unanesthetized–Gerbil Model of Cerebral Ischemia–induced Behavioral Changes, Journal of Pharmacological Methods 14, 137–146 (1985) Chandler, et al.
A Modified Bischler–Napieralski Procedure for the Synthesis of 3–Aryl–3,4–dihydroisoquinolines, J. Org. Chem. 1991, 56, 6034–6038, Larsen et al.
Reversal of age–related increase in brain protein oxidation, decrease in enzyme activity, and loss in temporal and spatial memory by chronic administration of the spin–trapping compound N–tert–butyl–α–phenylnitrone, Proc. Natl. Acad. Sci. USA vol. 88, pp. 3633–3636, May 1991 Neurobiology, Carney et al.
Tungstate–Catalyzed of Secondary Amines to Nitrones. α–Substitution of Secondary Amines via Nitrones; J. Org. Chem. 1990, 55, 1736–1744.
Baggiolini, M. et al, Chemical Abstracts vol. 111, No. 25 Abstract 230.179e, p. 565, Dec. 18, 1989.
Dinarello, et al, Chemical Abstracts vol. 105, No. 21, Abstract 189195t, p. 591, Nov. 24, 1986.

*Primary Examiner*—C. Warren Ivy
*Assistant Examiner*—Zinna N. Davis
*Attorney, Agent, or Firm*—J. Michael Dixon

[57] ABSTRACT

The present invention is directed to a new class of cyclic nitrones and their use as spin trapping agents.

25 Claims, 5 Drawing Sheets

CYCLIC NITRONES

This is a divisional of application Ser. No. 08/352,470, filed Dec. 9, 1994, now allowed which is a division of application Ser. No. 08/170,543, filed on Dec. 20, 1993, issued as U.S. Pat. No. 5,397,789 on Mar. 14, 1995, which is a division of application Ser. No. 07/926,109, filed on Aug. 5, 1992, issued as U.S. Pat. No. 5,292,746 on Mar. 8, 1994, which is a Continuation-In-Part of application Ser. No. 07/828,075, filed Jan. 30, 1992, now abandoned, which was a Continuation-In-Part of application Ser. No. 07/758,063, filed Sep. 12, 1991, now abandoned.

The present invention is directed to a new class of cyclic nitrones, their use in the prevention of oxidative tissue damage from oxygen based free radicals, their use in the treatment of a number of disease states in which oxygen radicals either damage or destroy tissues via oxidation, and pharmaceutical compositions containing these cyclic nitrones. Another aspect of this invention is directed to their use as interleukin-1 inhibitors.

BACKGROUND OF THE INVENTION

Molecules containing an unpaired electron are referred to as free radicals. Free radicals are extremely reactive. Partial reduction of oxygen by mammalian biological systems produces the free radicals, superoxide and hydroxyl. The two electron reduction product of oxygen, hydrogen peroxide, is also produced but contains no unpaired electrons. However, it is usually a precursor to the hydroxyl radical which is the most reactive of the three. The hydroxyl free radical will react with almost any biomolecule. Examples of such biomolecules include nucleic acids, lipids, and proteins. The hydroxyl radical will oxidize the biomolecule by either extracting a hydrogen atom from the biomolecule or by adding directly to the biomolecule itself. This oxidation by the hydroxyl free radical transforms the biomolecule into a radical which will readily react with molecular oxygen thereby forming what is referred to as a peroxyl free radical. The resulting peroxyl radical will react with another biomolecule producing a free radical which will also be transformed into another peroxyl radical as described above. The initial presence of the oxygen free radical initiates a chain reaction in which a number of biomolecules in the organism are oxidized. By oxidizing lipids, these free radicals can affect cell membranes, their permeability, ion channels, cell function, etc. By oxidizing proteins, they can alter enzymes, muscular function, nerves, etc. By oxidizing nucleic acids, they can affect DNA, RNA, and their expression products.

Recent research has indicated that excessive levels of these oxygen free radicals are associated with the tissue damage which occurs in a number of disease states such as stroke, myocardial infarction, senile dementia, shock, etc. Recent research has also shown that spin trapping agents may be utilized to terminate the reaction cascade described above, thereby preventing or minimizing any tissue damage. Oxygen free radicals and carbon centered radicals will react more readily with the spin trapping agent than with a biomolecule. The reaction with the spin trapping agent will result in the formation of a stable radical adduct and thus will terminate the chain reaction that is typically associated with oxygen radicals. Most tissue damage results from the chain reaction that is initiated by the oxygen radical rather than by the oxygen radical itself. The mechanism of action by which oxygen radicals cause tissue damage as well as the use of spin trapping agents to prevent this damage, is described more fully by Floyd, FASEB Journal, Vol. 4, page 2588 (1990).

DESCRIPTION OF THE INVENTION

In accordance with the present invention, a new class of spin trapping agents have been discovered which can be described by the following formula:

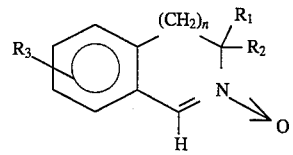

Formula I in which $R_1$ and $R_2$ are each independently represented by a $C_{1-3}$ alkyl, or $R_1$ and $R_2$ together form a $C_{2-7}$ alkylene chain; n is represented by an integer from 0–2; $R_3$ is represented by a substituent selected from the group consisting of hydrogen, halogen, $C_{1-4}$ alkyl, $C_{1-4}$ alkoxy, $-CF_3$, $-OCF_3$ and $-OH$; and the pharmaceutically acceptable basic addition salts thereof.

As used in this application:

a) the term "halogen" refers to a fluorine, chlorine, or bromine atom;

b) the term "$C_{1-4}$ alkyl" refers to a branched or straight chain alkyl group containing from 1–4 carbon atoms, such as methyl, ethyl, n-propyl, isopropyl, n-butyl, isobutyl, etc.;

c) the term "$C_{1-4}$ alkoxy" refers to a straight or branched alkoxy group containing from 1–4 carbon atoms, such as methoxy, ethoxy, n-propoxy, isopropoxy, n-butoxy, isobutoxy, etc., and;

d) the term "$C_{1-3}$ alkyl" refers to a straight or branched alkyl group containing from 1–3 carbon atoms, such as methyl, ethyl, n-propyl, isopropyl.

Some of the compounds of Formula I will exist as pharmaceutically acceptable basic additions salts. The expression "pharmaceutically acceptable basic addition salts" is intended to apply to any non-toxic organic or inorganic basic addition salts of the compounds represented by Formula I or any of its intermediates. Illustrative bases which form suitable salts include alkali metal or alkaline-earth metal hydroxides such as sodium, potassium, calcium, magnesium, or barium hydroxides; ammonia, and aliphatic, alicyclic, or aromatic organic amines such as methylamine, dimethylamine, trimethylamine, and picoline.

Some of the compounds of Formula I contain an asymmetric center and will exist as optical isomers. Any reference in this application to one of the compounds represented by Formula I is meant to encompass either a specific optical isomer or a mixture of optical isomers. The specific optical isomers can be separated and recovered by techniques known in the art such as chromatography on chiral stationary phases, or enzymatic hydrolysis using stereoselective esterases as is known in the art. Alternatively use of a particular optical isomer as the starting material will produce the desired isomer as the final product.

As is indicated by the definition for n, the cyclic nitrones of Formula I encompass several different heterocyclic rings. These various rings, their names and numbering is presented below to further illustrate the invention:

Structure 2

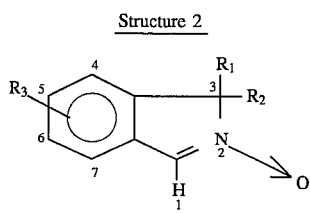

Formula I, n = 0
isoindole-N-oxide

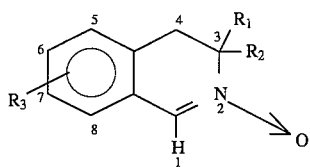

Formula I, n = 1
isoquinoline
(3, 4-dihydro)-N-Oxide

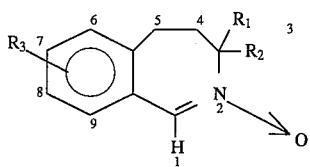

Formula I, n = 2
dihydrobenzazepine-N-oxide

As noted above, $R_1$ and $R_2$ may both be represented by $C_{1-3}$ alkyl. $R_1$ and $R_2$ may be represented by the same alkyl function or different alkyl functions. Alternatively $R_1$ and $R_2$ together may form an alkylene chain containing from 2–7 carbon atoms which may be represented by the formula $-(CH_2)_x-$, in which X is an integer from 2–7. Both the first and the last carbons in the alkylene chain will be bonded to position 3 of any of the heterocylics encompassed by Formula I.

As is indicated by the definitions for $R_3$, the benzo moiety of the heterocyclic ring may be further substituted by the non-hydrogen substituents specified. $R_3$ may represent up to 3 non-hydrogen substituents. These non-hydrogen substituents may be located at any of positions 4–7 of the isoindole ring, 5–8 of the isoquinoline ring, or 6–9 of the benzazepine ring.

Examples of compounds encompassed by Formula I include:

a) 3,4-dihydro-3,3-dimethylisoquinoline N-oxide and;

b) 3,4-dihydro-3,3-dimethyl-7-chloroisoquinoline N-oxide.

The compounds of Formula I can be prepared utilizing techniques that are analogously known in the art. Alternative methods of preparing these compounds are disclosed below in Reaction Scheme I:

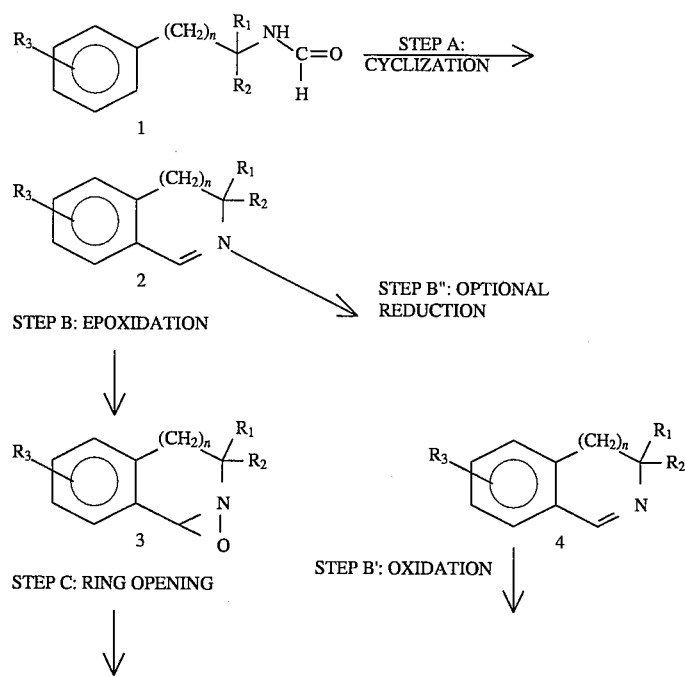

Reaction Scheme I

-continued
Reaction Scheme I

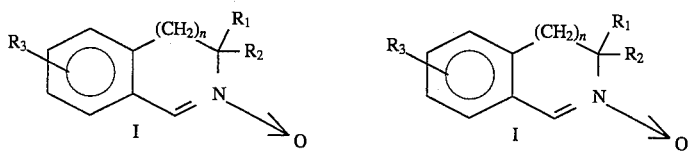

As is depicted above, the first step in the reaction scheme is to subject the phenylalkyl formamide of structure 1 to a cyclization reaction thereby forming the hetrocyclic derivative of structure 2. In Step B this heterocylic derivative is epoxidized thereby forming the oxaziridine derivative of structure 3. In Step C the oxaziridine ring is cleaved thereby forming the product of Formula I. Alternatively in Step B' the heterocyclic derivative of structure 2 is oxidized directly to the nitrone of Formula I. Step B' can also be modified by subjecting the heterocycle of structure 2 to an optional reduction reaction prior to carrying out the oxidation reaction.

The starting material in Reaction Scheme I is the phenylalkyl formamide of structure 1. Methods for producing these phenylalkyl formamides are known in the art. For example, see *Org. Syn.*, Vol. 44, pp 44–47 (1964). The appropriate starting material is one in which $R_1$, $R_2$, $R_3$, and n have the same meanings as in the desired product of Formula I.

The cyclization reaction of Step A can be carried out using techniques known in the art. Typically the phenylalkyl formamide is contacted with excess of a condensing agent such as phosphorous pentoxide, in an aprotic solvent such as toluene. The reactants are heated at reflux for a period of time ranging from 3 to 10 hours. Alternatively, $POCl_3/SnCl_4$ mixtures can be used to effect the same reaction. The resulting heterocyclic derivative of structure 2 can be isolated and purified using a variety of techniques known in the art. For example, after neutralization it may be recovered by extraction and purified by distillation.

Alternatively, the cyclization of Step A can be carried out in the following manner, which is described in more detail by Larsen, et al in *J. Org. Chem.*, Vol. 56; 1991, pp. 6034–6038. The phenylalkyl formamide is contacted with a slight excess of oxalyl chloride in an anhydrous chlorinated hydrocarbon solvent such as methylene chloride. The reactants are typically contacted at room temperature under an inert atmosphere for a period of time ranging from 0.5 to 2 hours. To the cooled reaction is added an excess of a Lewis acid, preferably $FeCl_3$. The reactants are stirred for a period of time ranging from 6 to 24 hours. Other Lewis acids such as $TiCl_4$, $SnCl_4$, or $AlCl_3$ may also be utilized instead. The reaction is typically washed with $H_2O$, dried with sodium sulfate and then concentrated. The crude product is then contacted with a strong mineral acid such as $H_2SO_4$ in methanol and heated at reflux for 6–12 hours. The product is recovered by extracting with an aqueous acid and subsequent neutralization. Alternatively, the crude intermediate product can be purified by chromatography using a suitable solvent system such as 50:50 ethyl acetate:hexane and the isolated intermediate can be converted to the heterocyclic structure 2 by heating neat at temperatures ranging from 100° to 150° C. for a period of time ranging from 0.25 to 1 hour. It may be subjected to one of the alternative reactions described below.

In Step B, the heterocyclic derivative of structure 2 is subjected to conditions used in a conventional epoxidation reaction, which produces the oxaziridine derivative of structure 3. The heterocyclic derivative of structure 2 is contacted with an excess of an oxidizing agent such as 3-chloroperbenzoic acid or peracetic acid. The reactants are contacted at depressed temperatures in a chlorinated hydrocarbon solvent such as dichloromethane. The oxidation is carried out for a period of time ranging from 2 to 8 hours. The resulting oxaziridine can be recovered and purified as is known in the art. For example, it may be recovered by concentration, and purified by silica gel chromatography and/or distillation.

In Step C, the desired product of Formula I is produced by opening the oxaziridine ring. This can be accomplished by cleavage techniques known in the art. One suitable method is to contact the oxaziridine derivative with a strong mineral acid, such as sulfuric acid, in an alcoholic solution for a period of time ranging from 3 to 10 hours. The reaction is typically run at room temperature, but may be heated if desired. The desired product of Formula I may be recovered and purified by techniques known in the art. For example, the reaction medium is neutralized, extracted with an organic solvent such as ether, and the organic layers are subjected to distillation. The product of Formula I may be further purified by chromatography or crystallization if desired.

The compounds of Formula I may be produced directly from the heterocylcic derivative of structure 2 as is depicted in Step B'. In this reaction, an alcoholic solution of the compound of structure 2 is contacted with a catalytic amount of sodium tungstate in the presence of excess aqueous hydrogen peroxide. The reaction is typically conducted in methanol at room temperature for a period of time ranging from 1 to 6 days. Methods for carrying out this reaction are described in more detail by Murahashi et al in *Organic Syntheses*, Vol. 70, pp. 265–271 (1991). The resulting product may be recovered and purified as described above in Step C.

Alternatively, heterocyclic derivatives of structure 2 can be reduced by treatment with 1.0 to 2.0 equivalents of an appropriate reducing agent such as sodium borohydride. Such reductions are typically accomplished in an alcoholic solvent such as methanol or ethanol at 20° C. for a period of time ranging from 1 to 12 hours to give reduced products of structure 4. These reduced products can be isolated by diluting the reaction with water or aqueous sodium hydroxide and extracting with dichloromethane. If necessary, the reduced products can be purified by chromatography. Compounds of structure 4 can then be oxidized using similar conditions to those described for Step B' except that the time of reaction is reduced to 1 to 24 hours.

The following examples further illustrate the reaction sequence described above. However, they should not be construed as limiting the invention in any manner.

EXAMPLE I

Example I 3,4-Dihydro-3,3-dimethylisoquinoline N-oxide

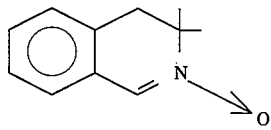

Step A)

3,4-Dihydro-3,3-dimethylisoquinoline

To a mechanically stirred solution of N-formyl-α, α-dimethyl-β-phenethylamine (33.4 g, 188 mmol) in toluene (325 mL, sieve dried) at room temperature was added phosphorous pentoxide (100 g, 705 mmol). The resulting mixture was refluxed for 6 hours and allowed to stand overnight at room temperature. The toluene was decanted off, the residue was treated with ice, and the resulting aqueous solution was washed twice with ether. The aqueous layer was basified with 50% NaOH solution to pH 8, and extracted three times with ethyl ether. The combined organic layers were washed twice with water, once with brine, dried (MgSO$_4$), treated with charcoal, filtered, and evaporated. The residue was distilled to afford 3,4-dihydro-3,3-dimethylisoquinoline (b.p. 71°–75° C., 0.2 mm) as a colorless oil.

Step B) 4,8b-Dihydro-3,3-dimethyl-3H-oxazirino[3,2a]isoquinoline

To a stirred solution of 3,4-dihydro-3,3-dimethyl-isoquinoline (1.0 g, 6.3 mmol) in dichloromethane (50 mL) at 0° C. was added 3-chloroperbenzoic acid (1.5 g of 80–85%, 7.0–7.4 mmol), portion wise, over a period of 3 min. After stirring 4 h at 0° C., the mixture was washed twice with saturated aqueous sodium bicarbonate, dried (MgSO$_4$), filtered, and concentrated to an oil. The oil was chromatographed on silica gel (50×160 mm), eluting with 20% hexane in ethyl acetate. The appropriate fractions were combined, concentrated, and the crude product distilled to afford a colorless oil (b.p. 105° C., 0.1 mm).

Step C)

3,4-Dihydro-3,3-dimethylisoquinoline N-oxide

To a stirred solution of 3,3-dimethyl-1,2,3,9-tetrahyrooxaziridine [3,2-a]isoquinoline (0.657 g, 3.75 mmol) in methanol (30 mL) and water (6 mL) was added sulfuric acid (24 mL), via pipet. After stirring overnight at room temperature, the solution was poured into aqueous sodium carbonate, and extracted three times with ether. The combined organic layers were washed with aqueous potassium dihydrogen phosphate, dried (MgSO$_4$), filtered, and concentrated. The residue was distilled to afford 3,4-dihydro-3,3-dimethylisoquinoline N-oxide (b.p. 156° C., 0.05 mm) as a colorless oil. The oil eventually crystallized to give solid, m.p. 70°–72° C.

EXAMPLE II

Step A )

7-Chloro-3,3-dimethyl-3,4-dihydro-isoquinoline

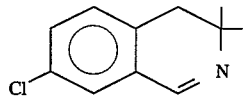

To a stirred solution of N-formyl-1-(4-chlorophenyl)-2-amino-2-methyl propane (9.36 g, 44.2 mmol) in dichloromethane (400 mL) under nitrogen was added oxalyl chloride (4.25 mL, 48.6 mmol) over 10 minutes. After 1 hour, the reaction was cooled in an ice-salt bath (–5° C.) and then treated with anhydrous ferric chloride (8.62 g, 53.0 mmol). One hour later, the cold bath was removed and the reaction stirred an additional 16 h. The dark reaction was then treated with 2.0M aqueous hydrochloric acid and stirred vigorously for 1 h. The organic layer was removed, washed with brine (100 mL), dried over Na$_2$SO$_4$, filtered and concentrated in vacuo, to an oil. This oil was dissolved in 1:19 concentrated sulfuric acid:methanol (400 mL) and heated at reflux for 6 h. The reaction was stirred overnight at room temperature, then concentrated in vacuo to about 30 mL. This was transferred to a separatory funnel, diluted with water (300 mL), and washed with ethyl acetate (200 mL). The ethyl acetate layer was extracted with 2.0M aqueous hydrochloric acid (2×100 mL) and the three combined acid layers were made basic with concentrated ammonium hydroxide. This was extracted with dichloromethane (3×200 mL) and the combined extracts were dried (Na$_2$SO$_4$) and concentrated in vacuo to a clear, very slightly colored oil (5.27 g). Rapid chromatography with ethyl acetate gave the title compound with an R$_f$=0.45, SiO$_2$, (ethyl acetate) as a slightly colored oil (5.22 g). $^1$H NMR (CDCl$_3$): 8.18 (1H,s), 7.33 (1H, dd, J=2.0, 8.0 Hz), 7.27 (1H, d, J=2.0 Hz), 7.08 (1H, d, J=8.0 Hz), 2.69 (2H, s), 1.24 (6H, s) ppm.

$^{13}$C NMR (CDCl$_3$): 156.33, 134.03, 132.68, 131.07, 129.59, 128.75, 127.17, 54.94, 37.10, 27.74 ppm.

Step B)

7-Chloro-3,3-dimethyl-3,4-dihydroisoquinoline-N-oxide

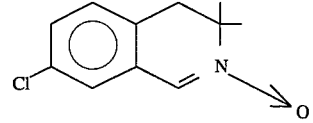

To a stirred solution of 7-chloro-3,3-dimethyl-3,4-dihydroisoquinoline (3.00 g, 15.5 mmol) in ethanol (25 mL) was added 30% aqueous hydrogen peroxide (3.2 mL, 32 mmol) followed by a solution of sodium tungstate dihydrate (1.02 g, 3.10 mmol) in water (10 mL). After 1 day at 20° C., water (5 mL) was added. After 1 day more, additional hydrogen peroxide (5.0 mL) and water (5 mL) were added. One day later, additional hydrogen peroxide solution was added (5 mL). After 3 more days, the reaction was treated with 30% aqueous sodium thiosulfite until starch-iodide paper showed the absence of hydrogen peroxide. Water (20 mL) was added and the reaction was extracted with dichloromethane (3×100 mL), the combined extracts dried (sodium sulfate), and concentrated in vacuo to an oil, partly solidifying on standing. Chromatography (ethyl acetate) gave a component with an R$_f$=0.25 as an oil, crystallizing on standing (2.67 g). This solid was recrystallized by dissolving in dichloromethane (8 mL), adding 10:90 ethyl acetate:hexane (20 mL), and concentrating on a steam bath to ca. 10 mL. On cooling, crystals formed. The very slightly orange crystals were isolated to give the title compound (2.25 g). m.p. 88°–89° C. Anal. calc. for C$_{11}$H$_{12}$ClNO: C, 63.01; H, 5.77; N, 6.68. Found: C, 62.87; H, 5.76; N, 6.47.

IR (KBr): 3439, 3018, 1580, 1544, 1488, 1266, 1240, 1191, 1175, 907, 746 cm$^{-1}$

CIMS (methane): 212 (34%), 211 (22%), 210 (100%), 209 (38%), 174 (22%).

$^1$H NMR (CDCl$_3$): 7.65 (1H, s), 7.23 (1H, dd, J=2.0, 8.0 Hz), 7.16 (1H, d, J=8.0 Hz), 7.11 (1H, d, J=2.0 Hz), 3.06

(2H, s), 1.54 (6H, s) ppm. $^{13}$C NMR (CDCl$_3$): 133.32, 132.64, 129.60, 129.12, 128.91, 128.19, 124.64, 67.32, 41.15, 24.62 ppm.

EXAMPLE III

Step A) 7-Fluoro-3,3-dimethyl-3,4-dihydroisoquinoline

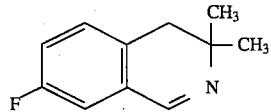

The title compound was prepared essentially as in Example II A except substituting N-formyl-1-(4-fluorophenyl)- 2-amino-2-methyl propane for the chloro-analog and refluxing with a sulfuric acid:methanol solution for 11 hours. Chromatography of the crude product with ethyl acetate gave title compound as a clear oil (R$_f$, SiO$_2$,=0.5, ethyl acetate).

$^1$H NMR (CDCl$_3$): 8.19 (1H, s), 7.12-6.96 (3H), 2.68 (2H, s), 1.24 (6H, s) ppm.

$^{13}$C NMR (CDCl$_3$): 161.83 (d, J=247 Hz), 156.39, 131.09 (d, J=3 Hz), 129.51 (d, J=7 Hz), 128.62 (d, J=7 Hz), 117.68 (d, J=19 Hz), 113.72 (d, J=22 Hz), 54.97, 36.88, 27.61 ppm.

Step B)

7-Fluoro-3,3-dimethyl-3,4-dihydroisoquinoline-N-oxide

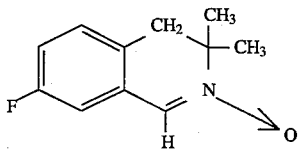

To a stirred solution of 7-fluoro-3,3-dimethyl-3,4-dihydroisoquinoline (1.00 g, 5.65 mmol) in ethanol (10 mL) was added 30% aqueous hydrogen peroxide (5.0 mL), pulverized sodium tungstate dihydrate (0.56 g, 1.7 mmol), and water (5 mL). After 1 day at 20° C., more aqueous hydrogen peroxide (2.5 mL) was added. After 3 days more, the reaction was cooled in an ice bath and treated with aqueous 30% sodium thiosulfite until starch-iodide test was negative. The reaction was extracted with dichloromethane (4×60 mL), dried (sodium sulfate) and concentrated in vacuo to an oil. Chromatography (ethyl acetate) gave a component (with an R$_f$=0.20,SiO$_2$,) isolated as an oil (0.83 g). Crystallization as in Example II, Step B, afforded the title compound as white crystals (0.495 g).

m.p.: 88°–90° C.

Anal. calc. for C$_{11}$H$_{12}$FNO: C, 68.38; H, 6.26; N, 7.25.

Found: C, 68.21; H, 6.26; N, 6.84.

IR (KBr): 3430, 3049, 2969, 1547, 1505, 1420, 1270, 1247, 1215, 1202, 1143, 814, 801 cm$^{-1}$.

CIMS (methane): 195 (15%), 194 (100%), 193 (30%), 174 (15%) $^1$H NMR (CDCl$_3$): 7.86 (1H, bs), 7.18 (1H, m), 7.00 (1H, dt), 6.89 (1H, dd), 3.08 (2H, s), 1.49 (6H, s). ppm:

$^{19}$F NMR (CDCl$_3$): −114.84 (broad quartet) ppm.

EXAMPLE IV

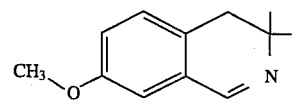

Step A) 3,3-Dimethyl-7-methoxy-3,4-dihydroisoquinoline

To a stirred solution of N-formyl-α,α-dimethyl-β-(p-methoxyphenyl) ethylamine (6.1 g, 29.4 mmol) in CH$_2$Cl$_2$ (230 mmol, anhydrous) under argon at RT was added oxalyl chloride (2.8 ml, 32.3 mmol). After 1 hour, the solution was cooled to −10° C. and treated with FeCl$_3$ (5.71 g, 35.3 mmol) in one portion. The ice bath was removed and the solution was stirred overnight.

The mixture was treated with aqueous HCl (200 ml, 3N) and stirred for 2 hours. The layers were separated and the organic layer was washed with brine, dried (MgSO$_4$), filtered and evaporated to a dark foam. The foam was dissolved in 5% H$_2$SO$_4$ in methanol (200 mL), refluxed for 6 hours and stirred over the weekend.

The mixture was concentrated and the residue was partitioned between H$_2$O and ether. The layers were separated and the ether layer was extracted twice with 2N HCl. The combined aqueous layers were made basic with 50% NaOH, and extracted twice with ether. The combined organic layers were washed with brine, dried (MgSO$_4$), filtered, and evaporated to afford 4.3 g of a yellow oil. The oil was distilled to afford a colorless oil (b.p 200° C. 0.15 mm).

Anal. Cald. for C$_{12}$H$_{15}$NO: C, 76.16; H, 7.99; N, 7.40 found: c, 74.87; H, 8.10; N, 7.73, Step B)

3,3-Dimethyl-7-methoxy-3,4-dihydroisoquinoline-N-oxide

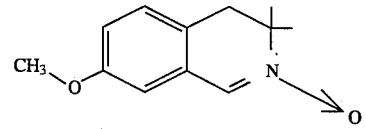

To a stirred solution of the product immediately above (2.0 g, 10.6 mmol) in ethanol (20 mL) was added H$_2$O$_2$ (2.3 mL of a 30% solution 22.3 mmol). Next, sodium tungstate (0.70 g, 2.1 mmol) was added in H$_2$O (10 mL). After stirring 48 hours at room temperature, additional H$_2$O$_2$ (11 mL) was added and the solution was stirred for the weekend.

The reaction was quenched by the addition of 10% sodium thiosulfate. After the mixture cooled it was transferred to a separatory funnel, diluted with water, and extracted twice with CH$_2$Cl$_2$. The combined organic layers were washed with brine, dried (MgSO$_4$), filtered, and evaporated to afford an oil.

The oil was chromatographed on silica gel (50×160 mm) eluting with 70% acetone in hexane to afford title compound as an oil. The oil was distilled to afford the title compound, b.p. 250° C., 0.2 mm. This material solidified on standing.

Anal. Cald. for C$_{12}$H$_{15}$NO$_2$ (205.26): C, 70.22; H, 7.37; N, 6.82.

Found: C, 70.14; H, 7.44; N, 6.53.

EXAMPLE V

Step A)

Spiro [cyclohexane-1,3]-3,4 dihydroisoquinoline

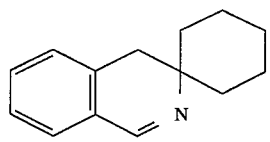

To a solution of 1.8 g (8.3 mmol) of 1-benzyl-1-formamidocyclohexane in 100 mL of dichloromethane under nitrogen atmosphere was added 1.1 g (9.1 mmol) of oxalyl chloride. The clear, colorless solution was stirred at room temperature for 1 hour and then cooled to 0° C., ferric chloride, 1.6 g (9.9 mmol), was added in a single portion and the reaction mixture was allowed to warm slowly to room temperature over 18 hours. To the dark mixture was added 80 mL of aqueous 10% hydrogen chloride and stirring was continued for 2 hours at room temperature. The reaction mixture was extracted with dichloromethane, the organic layer was dried with magnesium sulfate, filtered and concentrated to deliver a thick, dark oil which was diluted with 100 mL of 95:5 methanol-sulfuric acid solution and refluxed for 24 hours. The reaction mixture was cooled, concentrated on a rotary evaporator, diluted with water and extracted with ethyl acetate. The organic layer was washed with aqueouis 10% hydrogen chloride and discarded. The combined acidic aqueous layers were basified with concentrated ammonium hydroxide and extracted with dichloromethane. This organic layer was dried with magnesium sulfate and concentrated to yield 1.4 g (7.0 mmol) of a thick yellow oil. H-NMR (CDCl$_3$) δ 8.23 s(1H), 7.25, (4H), 2.70 s(2H), 1.56 m(10H).

Step B )

Sprio [ cyclohexane-1,3']-3,4-dihydroisoquinoline-N-oxide

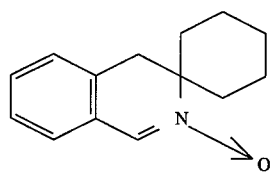

To a solution of 1.3 g (6.5 mmol) of spiro[cyclohexane-1,3']-3,4-dihydroisoquinoline in 10 mL of ethanol was added 20 mL of aqueous 30% hydrogen peroxide and 65 g (2.0 mmol) of sodium tungstate. After stirring for 48 hours at room temperature, the reaction mixture was cooled to 0° C. and diluted with 200 mL of aqueous 30% sodium thiosulfite. After stirring for 0.5 hours, the mixture was extracted with ethyl acetate. The organic layer was dried with magnesium sulfate, filtered and concentrated to yield a yellow solid that was chromatographed on silica gel (1:1 butanone:hexane eluent). The resulting solid was recrystallized from ethyl acetate and hexane to deliver 0.7 g of a white solid. mp 155°–7° C.

EXAMPLE VI

Step A)

Spiro [cyolopentane-1,3']-[1H]dihydroisoquinoline

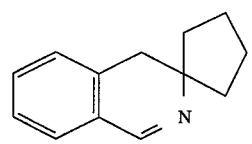

In an analogous manner to Example V, Step A, 1.3 g (7.0 mmol) of product was prepared from 1.5 g (7.4 mmol) of N-(1-benzylcyclopentyl ) formamide H-NMR (CDCl$_3$) δ 8.24 s(1H), 7.30 m(4H), 2.78 s(2H), 1.7 m(8H).

Step B)

Spiro [cyclopentane-1,3']-[1H]dihydroisoquinoline 2-oxide

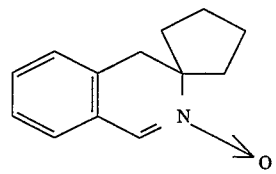

In an analogous manner to Example V, Step B, 1.6 g (8.0 mmol) of product was prepared having a m.p. of 119°–121° C.

EXAMPLE VII

Utilizing the procedure of Example I, steps A–C, or Example II, steps A–B, but substituting the appropriate phenylalkyl formamide of Structure 1 as the starting material, the following compounds are obtained:

A) 6-Chloro spiro [cyclopentane-1,3']-[1H]isoindole-N-oxide

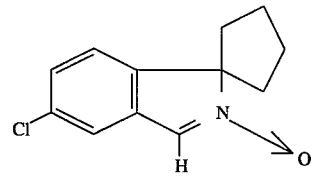

B) 7-Fluoro spiro [cyclohexane-1,3']-3,4-dihydroisoquinoline-N-oxide

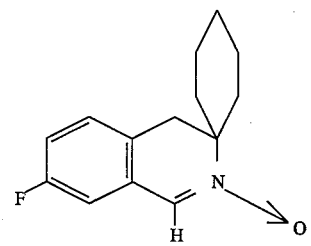

C) 3,3-Dimethyl-7-trifluoro methyl-3,4-dihydroisoquinoline-N-oxide

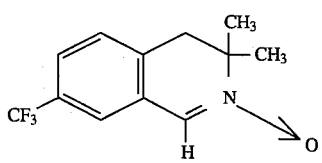

D) 3,3-Dimethyl-7-hydroxy-3,4-dihydroisoquinoline-N-oxide

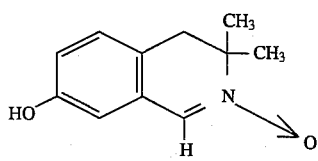

E) Spiro [cyclopentane-1,1'-[1H] isoindole-N-oxide

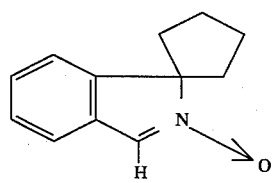

F) 3,3-Dimethyl-[1H] Isoindole-N-oxide

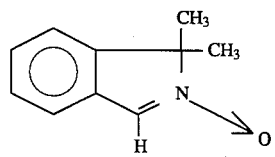

EXAMPLE VIII

A) 5-Chloro-3,3-dimethyl-3,4-dihydroisoquinoline-N-oxide

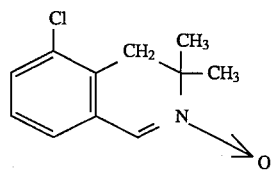

To a solution of 5-chloro-3,3-dimethyl-3,4-dihydroisoquinoline (2.53 g, 13 mmol) in dry methanol (45 mL) was slowly added sodium borohydride (0.99 g, 26 mmol). After 3 hours at ca. 20° C., the reaction was treated with aqueous 1.0M sodium hydroxide (45 mL) and stirred vigorously for 1 hour. After dilution with water (50 mL), the reaction was extracted with dichloromethane (3×70 mL) and the combined extracts were dried with sodium sulfate and concentrated in vacuo to a nearly colorless oil (2.56 g). A portion of this oil (2.00 g) was dissolved in ethanol (12 mL) and treated with a solution of sodium tungstate dihydrate (0.167 g) in water (8 mL). The stirred reaction was cooled in an ice bath and treated with aqueous 30% hydrogen peroxide (exothermic). After 1 hour the cold bath was removed and after 2.5 hours at. ca. 20° C. the reaction was diluted with water (50 mL), extracted with dichloromethane (2×120 mL), dried over sodium sulfate, and concentrated in vacuo to an oil. This oil was chromatographed on silica using 50:50, then 100:0 ethyl acetate:hexane, then 10:90 ethanol:ethyl acetate, isolating the component with an $R_f$ of ca. 0.4 in the initial eluant. This white, crystalline solid was the title compound (2.05 g).

Melting point: 104.5°–106.0° C.

Anal. calc. for $C_{11}H_{12}ClNO$: C, 63.01; H, 5.77; N, 6.68.

Found: C, 62.92; H, 5.76; N, 6.57.

IR (KBr): 2968, 1571, 1537, 1463, 1444, 1291, 1262, 1243, 1175, 921 cm$^{-1}$.

EIMS: 209 (100%), 177 (88%).

$^1$H NMR (CDCl$_3$): 8.10 (1H, s), 7.28 (1H, d, J=7.6 Hz), 7.18 (1H, t, J=7.6 Hz), 7.09 (1H, d, J=7.5 Hz), 3.08 (2H, s), 1.46 (6H, s) ppm.

$^{13}$C NMR (CDCl$_3$): 131.86, 129.43, 129.37, 129.32, 128.39, 126.27, 125.93, 66.86, 42.05, 24.57 ppm.

B) 3,3-Dimethyl-4,5-dihydro-3H-2-benzazepine-1-oxide

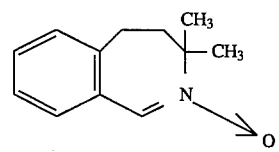

The title compound was made as described in Example II except the intermediate product was purified by chromatography using 50:50 ethyl acetate:hexane to isolate the component with an $R_f$ of ca. 0.5. This solid was converted to the required imine by heating under nitrogen at 140°–145° C. until gas evolution had ceased. After cooling, the unpurified imine was carried on as described in Example VIII A to give the title compound as a white solid.

Melting point: 62°–65° C.

Anal. calc. for $C_{12}H_{15}NO$: C, 76.16; H, 7.99; N, 7.40.

Found: C, 75.85; H, 8.21; N, 7.27.

CIMS (methane): 190 (100%).

IR (KBr): 2980, 2951, 1543, 1159, 1146, 1130, 662 cm$^{-1}$.

$^1$H NMR (CDCl$_3$): 7.91 (1H, s), 7.28-7.15 (4H, m), 3.05-3.01 (2H, m), 2.21-2.17 (2H, m), 1.63 (6H, s) ppm.

$^{13}$C NMR (CDCl$_3$): 140.54, 139.52, 131.59, 129.11, 128.83, 128.07, 126.67, 72.66, 37.97, 29.88, 28.17 ppm.

C) 8-Chloro-3,3-dimethyl-3,4-dihydroisoquinoline-N-oxide

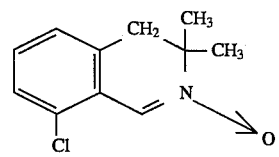

The title compound was prepared as described in Example VIII A except using the appropriate dihydroisoquinoline as the starting material. The product was isolated as a white solid.

Melting point: 109.5°–111.0° C.

Anal. calc. for $C_{11}H_{12}ClNO$: C, 63.01; H, 5.77; N, 6.68.

Found: C, 62.85; H, 5.75; N, 6.66.

IR (KBr): 2981, 1542, 1274, 1175, 1119 cm$^{-1}$.

EIMS: 209 (100%), 177 (82%)

$^1$H NMR (CDCl$_3$): 7.67 (1H, s), 7.31 (1H, dd, J=1.2, 8.1 Hz), 7.20 (1H, dd, J=7.5, 8.1 Hz), 7.01 (1H, d, J=7.5 Hz), 3.19 (2H, s), 1.48 (6H, s) ppm.

$^{13}$C NMR (CDCl$_3$): 133.38, 131.64, 130.11, 129.63, 128.43, 127.63, 123.08, 66.97, 38.92, 24.91 ppm.

Step D 6,8-Dichloro-3,3-dimethyl-3,4-dihydroisoquinoline-N-oxide

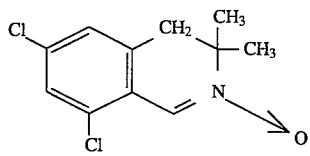

The title compound was prepared as described in Example VIII A except using the appropriate dihydroisoquinoline. It was isolated as a white solid.

Melting point: 92.0°–94.0° C.

Anal. calc. for C$_{11}$H$_{11}$C$_{12}$NO: C, 54.12; H, 4.54; N, 5.74

Found: C, 54.26; H, 4.51; N, 5.85.

IR (KBr): 1570, 1533, 1460, 1293, 1256, 1221, 1169, 1093, 936, 860 cm$^{-1}$.

EIMS: 245 (63%), 243 (100%), 213 (65%), 211 (90%), 178 (40%), 176 (63%).

$^1$H NMR (CDCl$_3$): 8.03 (1H, s), 7.31 (1H, d, J=2.0 Hz), 7.11 (1H, dd, J=0.7, 1.8 Hz), 3.05 (2h, s), 1.46 (6H, s) ppm.

$^{13}$C NMR (CDCl$_3$): 134.26, 132.91, 129.77, 128.69, 128.30, 126.35, 124.98, 66.88, 41.86, 24.55 ppm.

Step E

6-Chloro-3,3-dimethyl-3,4-dihydroisoquinoline-N-oxide

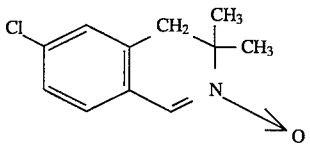

The title compound was prepared as described in Example VIII A except using the appropriate dihydroisoquinoline. It was isolated as a white solid.

Melting point: 64.5°–66.5° C.

Anal. calc. for C$_{11}$H$_{12}$ClNO: C, 63.01; H, 5.77; N, 6.68.

Found: C, 62.91; H, 5.83; N, 6.53.

IR (KBr): 3018, 1583, 1544, 1269, 1241, 1189, 1176, 564, 521 cm$^{-1}$.

EIMS: 211 (37%), 209 (100%), 179 (40%), 177 (92%).

$^1$H NMR (CDCl$_3$) 7.67 (1H, s), 7.24 (1H, dd, J=2.0, 8.1 Hz), 7.20 (1H, bs) 7.05 (1H, d, J=8.1 Hz), 3.06 (2H, s), 1.45 (6H, s) ppm.

$^{13}$C NMR (CDCl$_3$): 134.41, 131.62, 131.53, 127.80, 127.64, 126.98, 125.58, 66.83, 41.53, 24.60 ppm.

EXAMPLE IX

A) Spiro[cyclohexane-1,3']-3,4-dihydroisoquinoline-N-oxide

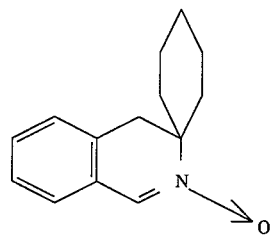

A solution of 5.0 g (25.1 mmol) of spiro [cyclohexane-1,3']-(4'H)-isoquinoline in 200 mL of methanol was treated with 1.90 g (50.2 mmol) of sodium borohydride and stirred for 3 hours at room temperature. The reaction mixture was concentrated, treated with 100 mL of 1N sodium hydroxide and extracted with dichloromethane. The organic layer was dried and concentrated to yield 4.5 g of a thick oil which was immediately diluted with 100 mL of methanol and treated with 7.3 mL of 30% hydrogen peroxide and a catalytic amount of sodium tungstate. After 3 hours at room temperature the reaction was concentrated, treated with aqueous sodium bisulfite and extracted with dichloromethane. The organic layer was dried and concentrated to deliver a solid which was recrystallized from dichloromethane/cyclohexane 3.51 g Melting point: 152°–155° C.

In an analogous manner the following were prepared:

B) Spiro[cyclohexane-1,3']-7-chloro-3,4-dihydro isoquinoline-N-oxide

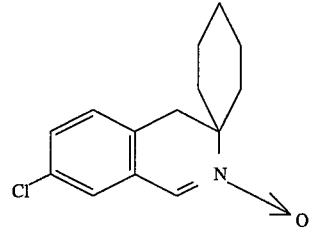

6.0 g (25.6 mmol) of Spiro[cyclohexane-1,3]-7-chloro-3,4-dihydroisoquinoline was prepared as the crude and 2.79 g of the desired product, mp 127°–130° C., was recrystallized from dichloromethane/hexanes.

C) Spiro[cyclohexane-1,3']-6-methoxy-3,4-dihydro isoquinoline-N-oxide

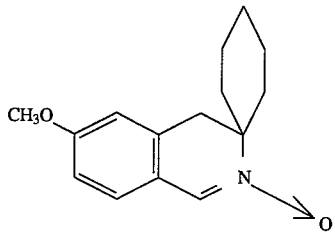

1.8 g (7.9 mmol) of Spiro[cyclohexane-1,3]-6-methoxy-3,4-dihydro isoquinoline was prepared as the crude and 1.2 g of the desired product, melting point 102°–104° C., was recrystallized from dichloromethane/hexanes.

D) Spiro[cyclohexane-1,3']-8-methoxy-3,4-dihydro-isoquinoline-N-oxide

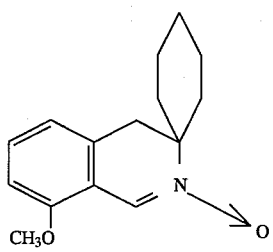

1.3 g (5.6 mmol) of Spiro[[cyclohexane-1,3']-8-methoxy-3,4-dihydroisoquinoline were prepared as the crude and 0.56 g of the purified product was obtained by Kugelrohr distillation at 1 mm Hg and 250° C. $^1$H-NMR (CDCl$_3$) 8.09 (s, 1H), 7.22 (m, 1H), 6.8 (m, 2H), 3.85 (s, 3H), 3.12 (s, 2H), 2.24 (m, 2H), 17 (m, 5H), 1.4 (m, 3H) (thick oil that did not solidify).

EXAMPLE X

A) 3,3-Dimethyl-6,7-dimethoxy-3,4-dihydroisoquinoline-N-oxide

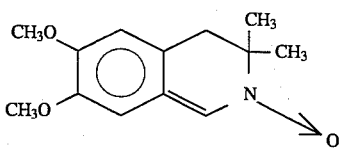

The title compound was made as described in Example IV B except 3,3-dimethyl-6,7-dimethoxy-3,4-dihydroisoquinoline was utilized as the starting material. The title compound was obtained by distillation b.p. 250° C., 0.07 mm Hg.

B) 3,3-Dimethyl-6-methoxy-3,4-dihydroisoquinoline-N-oxide

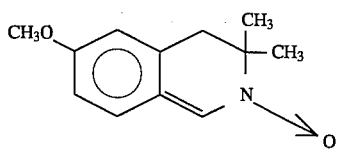

The title compound was prepared analogously to Example VIII A utilizing the appropriately substituted isoquinoline analog. The title compound was obtained as an oil (b.p. 225° C., 0.1 mm Hg) which solidified upon standing mp 77°–78° C.

C) 3,3-Dimethyl-8-methoxy-3,4-dihydro isoquinoline

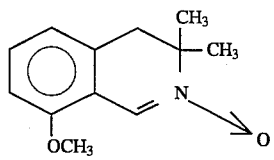

The title compound was prepared analogously to Example VIII A utilizing the appropriately substituted isoquinoline analog. The title compound was obtained as an oil (b.p. 230° C., 0.5 mm) which solidified upon standing mp 104°–106° C.

The compounds of Formula I are spin trapping agents. They may be utilized to treat diseases in which oxygen or peroxyl free radicals cause tissue damage. The compounds will either prevent or significantly decrease the amount of tissue damage that occurs.

The compounds ability to trap oxygen free radicals and carbon centered radicals and to prevent the oxidation of biomolecules can be demonstrated by in vitro assays known in the art. One such assay is based upon the fact that the lipid, soybean phosphatidylcholine, readily undergoes oxidation. This oxidation may be initiated by a variety of oxidizing agents such as $Fe^{2+}$ and $H_2O_2$, or 2,2'-azobis-(2-amidinopropane). A spin trapping agent will decrease the rate at which the lipid undergoes oxidation in this assay. This assay is described in detail in: a) Nilsson, U. A., Olsson, L-I, Carlin, G. and Bylund-Fellenius, A-C. (1989) Inhibition of lipid peroxidation by spin labels. Relationships between structure and function. J. Biol. Chem. 264:11131–11135; and b) Aust, S. D. (1985). Lipid peroxidation. In Handbook of Methods for Oxygen Radical Research. (Greenwald, R. A., ed.) CRC Press, Inc. Boca Raton, Fla., pp. 203–207.

Another assay is based upon the fact that hydroxyl free radicals will bleach p-nitrosodimethylaniline. A spin trapping agent will decrease the amount of bleaching that occurs. This assay is described in: a) Bors, W., Michel, C., and Saran, M. (1979) On the nature of biochemically generated hydroxyl radicals. Studies using the bleaching of p-nitrosodimethylaniline as a direct assay method. Eur. J. Biochem. 95:621–627

The results of one such assay are presented below. Soybean phosphatidylcholine (PC) was obtained from commercial suppliers such as Sigma or Avanti Polar Lipids. The soy PC was dissolved in ethanol achieving a final concentration of 0.563 mM. The ethanol/PC solution (80 ul) was added to 8 ml of 50 mM NaCl/10 mM Tris buffer, pH 7.0 with mixing at 37° C. thereby obtaining a liposome.

The ability of a compound to inhibit oxidation of the soy PC liposome was evaluated in the following manner. Oxidation was initiated with hydrogen peroxide and $Fe^{2+}$. The test was carried out at 37° C. in a metabolic shaker. 8Ml of the liposome, hydrogen peroxide (final conc of 50 uM), $Fe^{2+}$ (final conc. of 50 uM), the test compound, and buffer were added to the test vehicle until a final volume of 9 ml was obtained.

The oxidation was carried out under an air atmosphere for 15 minutes. The assay was essentially carried out using the protocol of Augt, Supra, which is summarized as follows. One ml aliquots were removed at 0, 2, 4, 6, 8, 10, 12, and 15 minutes and added individually to 2 ml of 0.67% thiobarbituric acid: 10% tricholoracetic acid (2:1) in 0.25N HCL, containing 2% BHT to terminate oxidation.

The samples were heated at 100° C. for 20 minutes, cooled and centrifuged. The absorbance of the resulting supernatant was determined at 532–580nm. Quantitation of the thiobarbituric acid/oxidized PC complex was determined by comparison to a standard curve of malondialdehyde equivalents generated by acid catalysed hydrolysis of 1,1, 3,3-tetraethoxypropane. The results were expressed as the amount of compound required to inhibit 100% of the oxidation of the soy liposome ($IC_{100}$) over the 15 minute time period. The following results were obtained.

TABLE I $IC_{100}$ Required to prevent Oxidation of Soybean Phosphatidylcholne by $Fe^{+2}/H_2O_2$

| $R_3$ | $R_1$ | $R_2$ | $R_1 + R_2$ | IC100 (mM) |
|---|---|---|---|---|
| H | $CH_3$ | $CH_3$ | — | 1.5 |
| 7-$OCH_3$ | $CH_3$ | $CH_3$ | — | 1 |
| 7-Cl | $CH_3$ | $CH_3$ | — | 0.2 |
| 7-F | $CH_3$ | $CH_3$ | — | 0.5 |
| 6,7-$(OCH_3)_2$ | $CH_3$ | $CH_3$ | — | >2.5 |
| H | — | — | $-(CH_2)_4$ | 0.3 |
| H | — | — | $-(CH_2)_5$ | 0.1 |

The procedure described above was repeated utilizing $Fe^{2+}$/histidine-$Fe^{3+}$ to oxidize the soy PC. The histidine-$Fe^{3+}$ was prepared as a stock solution of (25:5mM) buffer system described above. The histidine/$Fe^{+3}$ was present in the test beaker at a concentration of 250:50 uM and the oxidation was initiated with 50 uM of $Fe^{2+}$. The test protocol was otherwise not altered.

TABLE II $IC_{100}$ Required to prevent Oxidation of Soybean Phosphatidylcholne by $Fe^{+2}$/histidine-$Fe^{3+}$

| $R_3$ | $R_2$ | $R_1$ | $R_1 + R_2$ | $IC_{100}$ (mM) |
|---|---|---|---|---|
| H | $CH_3$ | $CH_3$ | — | 2.5 |
| 7-$OCH_3$ | $CH_3$ | $CH_3$ | — | 2 |
| 7-Cl | $CH_3$ | $CH_3$ | — | 0.5 |
| 7-F | $CH_3$ | $CH_3$ | — | 1.5 |
| 6,7-$(OCH_3)_2$ | $CH_3$ | $CH_3$ | — | >4 |
| H | — | — | $-(CH_2)_4$ | 0.7 |
| H | — | — | $-(CH_2)_5$ | 0.3 |
| 5-Cl | $CH_3$ | $CH_3$ | — | 0.3 |
| 6-Cl | $CH_3$ | $CH_3$ | — | 0.3 |
| 8-Cl | $CH_3$ | $CH_3$ | — | 0.3 |
| 6,8-Cl | $CH_3$ | $CH_3$ | — | 0.05 |
| 7-Cl | — | — | $-(CH_2)_5$ | 0.05 |
| 6-$OCH_3$ | — | — | $-(CH_2)_5$ | 0.25 |
| 8-$OCH_3$ | — | — | $-(CH_2)_5$ | 0.10 |

One of the primary therapeutic uses of these compounds will be in the treatment of stroke. Strokes are associated with cerebral ischemia. Initially, it was thought that the CNS damage that often accompanies a stroke was a direct result of the tissues being deprived of oxygen. Recent research has shown that most of the damage occurs when the tissues are reoxygenated during reperfusion. McCord et al has demonstrated that free radicals are produced during reperfusion of ischemic tissues. Gastroenterology, 82, 9–15 (1982). Oliver et al has shown that a significant amount of this damage occurs due to free oxygen radicals and the oxidation sequence which they initiate, Proc. Natl. Acad. Sci. USA, vol. 87, pp 5144–5147 July 1990. Floyd has demonstrated that the spin trapping agent, α-phenyl N-tert-butyl nitrone (PBN), minimized tissue damage in a gerbil model of stroke, supra. In this model the carotid arteries of gerbils are constricted surgically and after a predetermined period, the constriction is removed so that surrounding tissues may be reperfused. CNS damage, which occurs upon reperfusion, can be measured by the level of protein oxidation that occurs in the brain or by examining the gerbil's behavior. Animals receiving PBN experienced less CNS damage than the control animals. Oliver et al and Phillis et al have also shown similar results with PBN, supra and Neuroscience Letter, 116 (1990) 315–319.

Since the compounds of Formula I are spin trapping agents, they may be utilized in the treatment of stroke. The compounds efficacy in treating stroke can also be demonstrated in the gerbil model described immediately above.

The compound, 3,4-dihydro-3,3-dimethylisoquinoline N-oxide which was the product of Example I (hereinafter compound) was tested in a gerbil model as described above. The exact procedure utilized is described by Chandler et al. in Journal of Pharmacological Methods Vol. 14, pages 137–146 (1985). FIGS. I–V summarize the results that were obtained.

BRIEF DESCRIPTION OF THE FIGURES

Gerbils subjected to cerebral ischemia exhibit a characteristic behavior pattern such as drastically increased locomotor activity. FIG. I depicts the effect the compound had on the motor activity of non-ischemic gerbils. Examination of FIG. I demonstrates that the compound had no effect upon the locomotor activity of non-ischemic gerbils.

FIG. II depicts the effects that ischemia has upon the gerbils locomotor activity. This data demonstrates that ischemia significantly increased the gerbil's locomotor activity.

Figure 1:
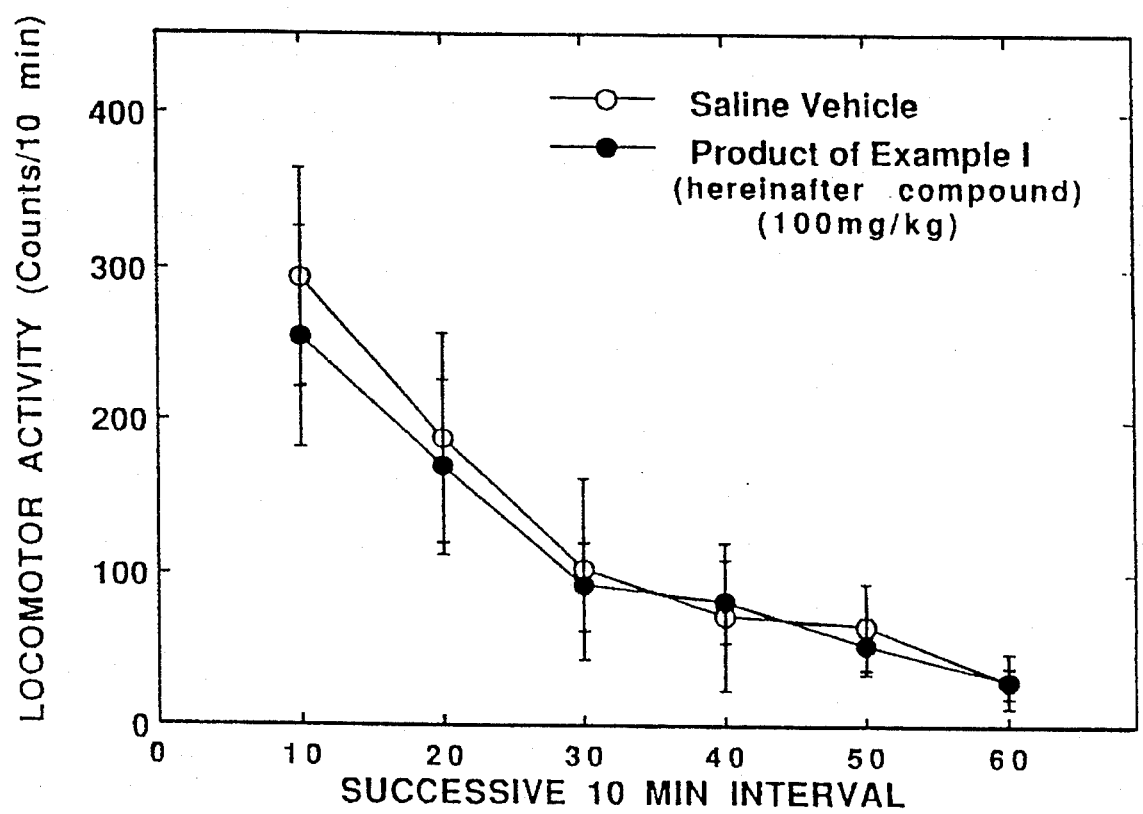
Figure 2:
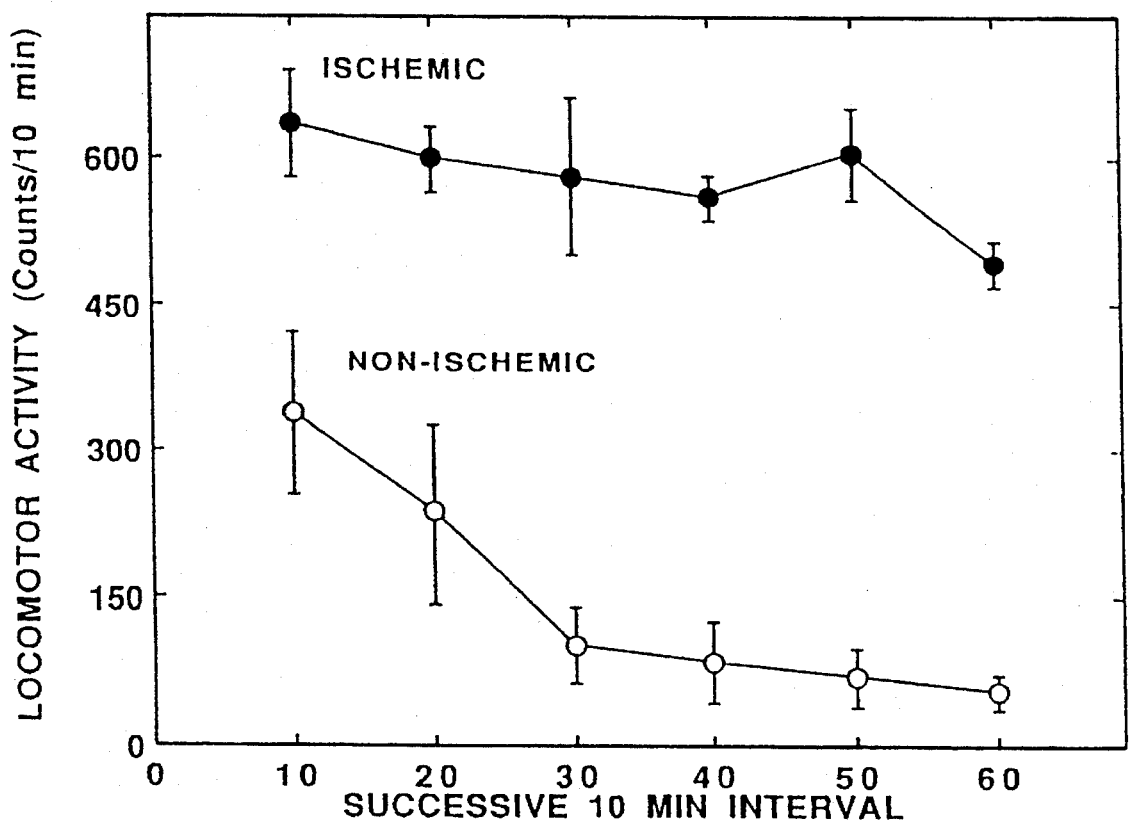
Figure 3:
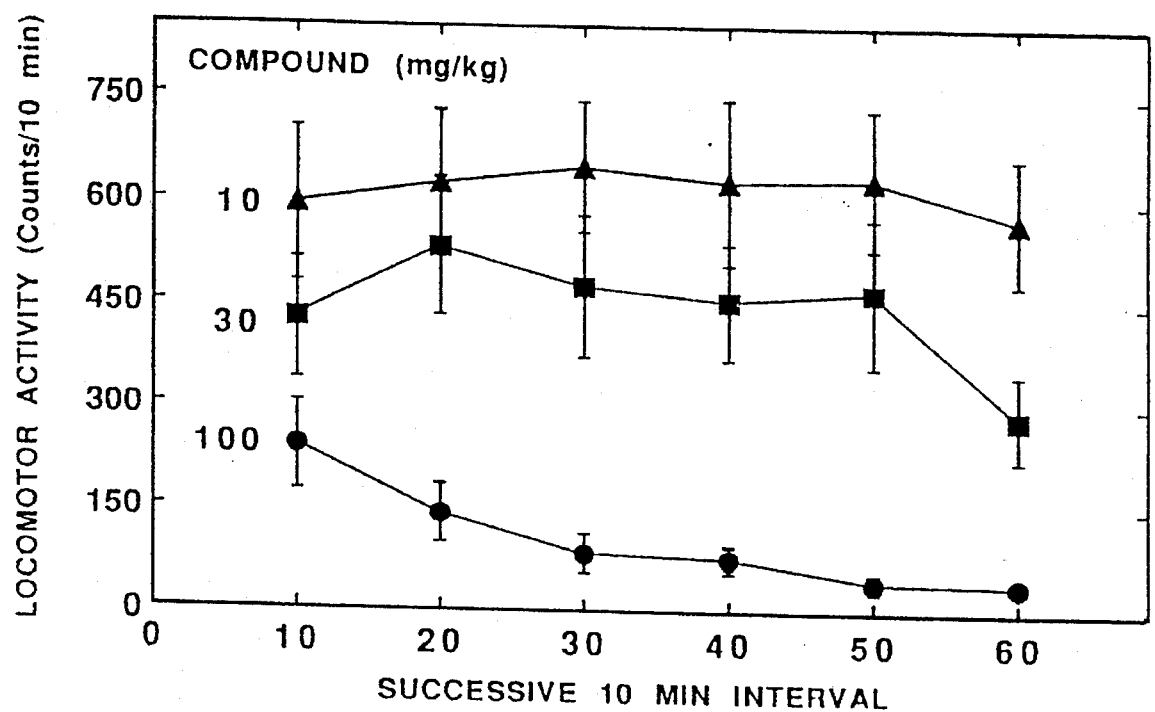
Figure 4:
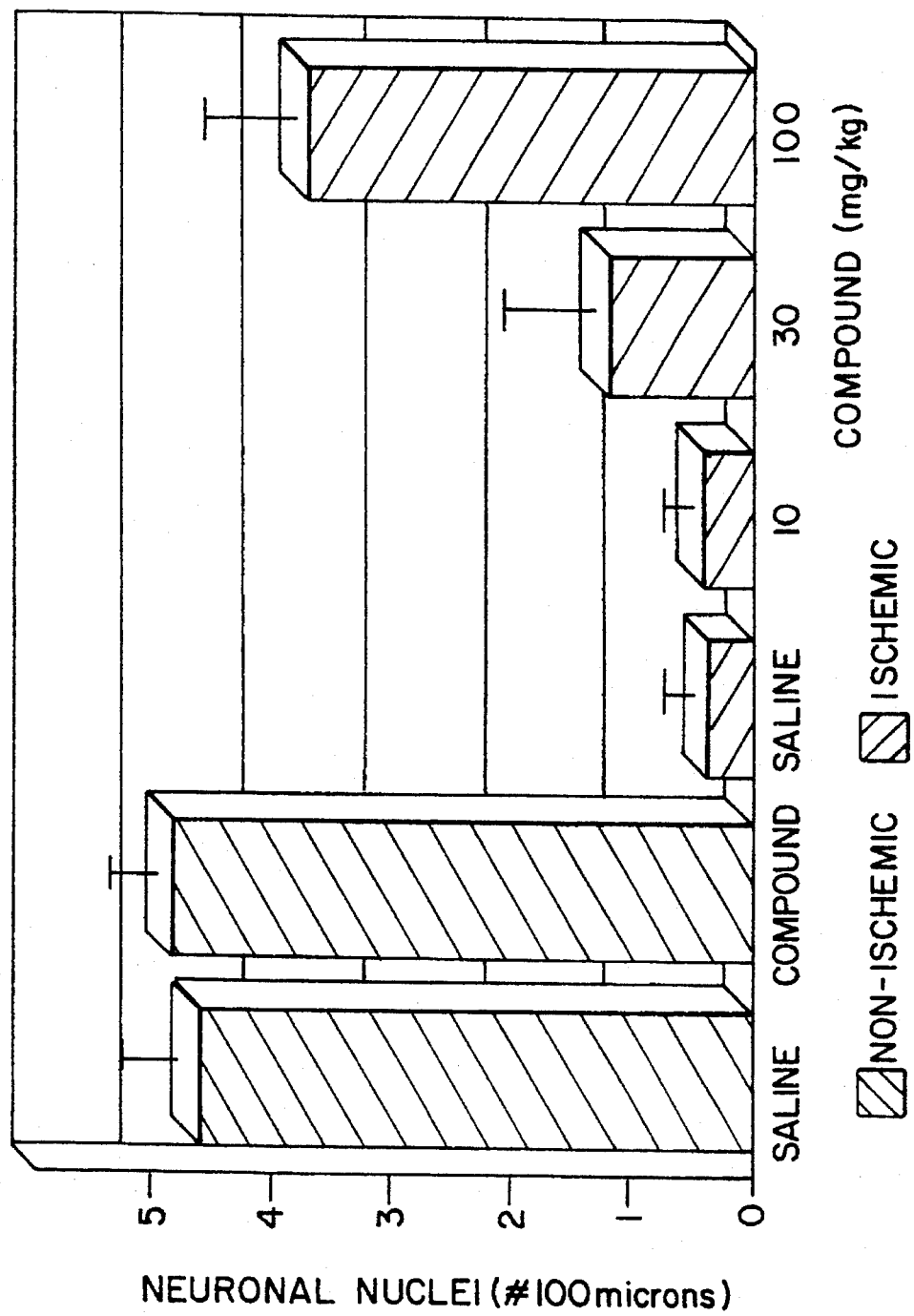
Figure 5:
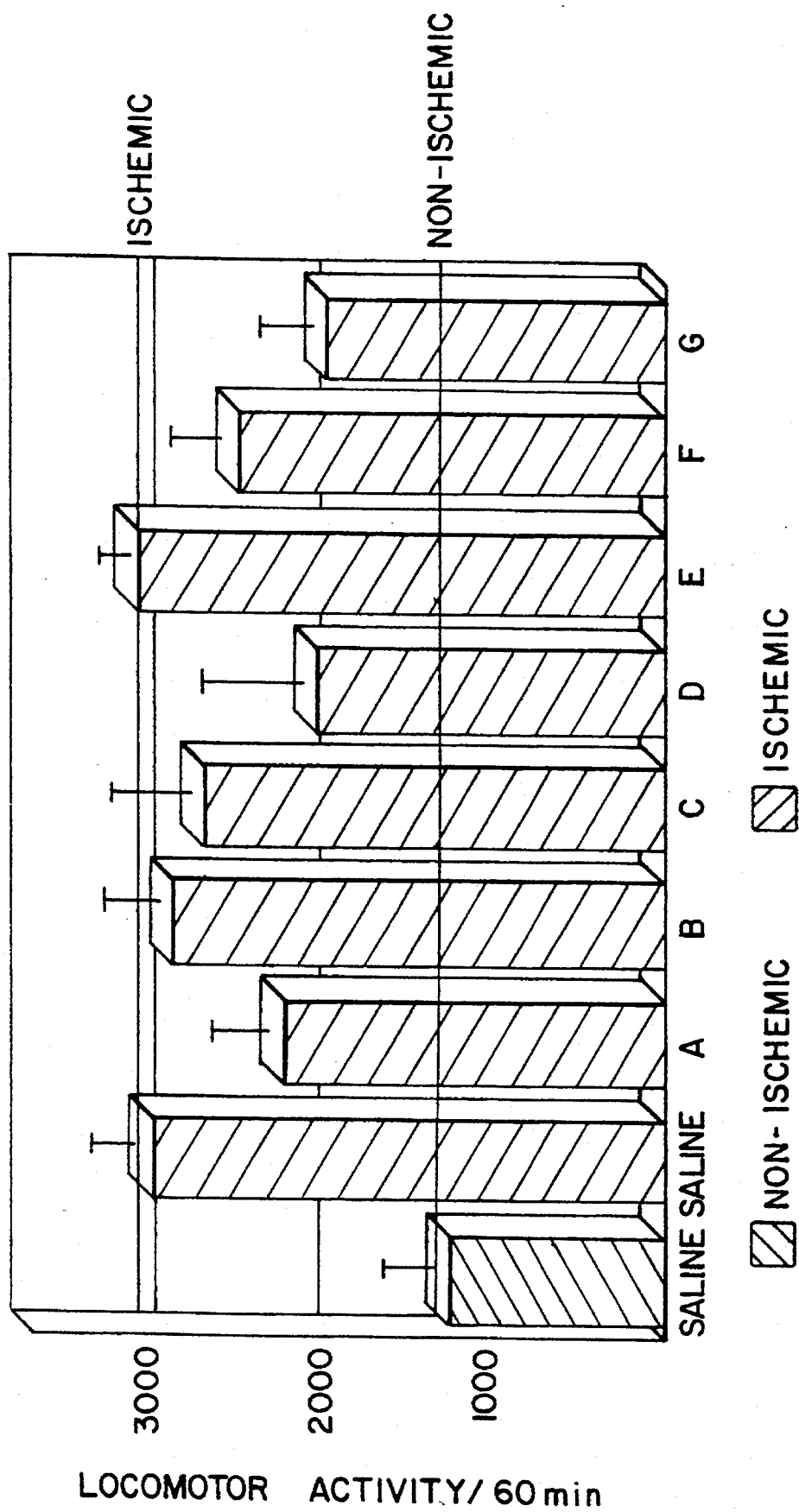

FIG. III shows the neuroprotective effect that the compounds exhibited. The gerbils were pretreated with the compound 30 minutes prior to initiation of the ischemic event. At 30 mg/kg and 100 mg/kg, the compound significantly decreased the locomor activity of these rodents which is indicative of preserving neuronal tissues.

FIG. IV compares the neuronal loss of ischemic gerbils receiving various doses of compound with both control gerbils and non-ischemic gerbils. This data demonstrates that the compound saved significant amounts of neuronal tissue at appropriate doses.

FIG. V demonstrates the protective effect of other compounds encompassed by Formula I in this gerbil model. All compounds were administered at 32 mg/kg. The protective effect could be enhanced by administering the compounds at higher doses. Compound A represents the product of Example I, B=Example III, C=Example II, D=Example IV; E=Example XA, F=Example VI, and G=Example V.

The compounds of Formula I can be utilized to prevent reperfusion induced tissue damage in other ischemic conditions besides stroke. Patients suffering a myocardial infarction experience ischemia of myocardial tissues. This ischemia is often associated with destruction of myocardial muscle cells and a corresponding decrease in the contractility of the myocardium. Recent research has also shown that a significant amount of this damage occurs at the time of reperfusion. Bolli et al has shown that oxygen radicals are generated during reperfusion of myocardial tissues and that PBN decreases the amount of myocardial dysfunction occurring after reperfusion, Free Rad. Res. Comms., Vol. 9, No. 3–6, pp 169–180. Reperfusion damage may also occur in hepatic, kidney and gut tissues. Reperfusion damage is also associated with the pressure sores (bed sores) which commonly afflict bed ridden patients.

The compounds of Formula I may be utilized to prevent the oxidative damage that typically accompanies the reperfusion of ischemic tissues. In order to exhibit this effect, it is necessary for the compounds to be administered within 8 hours of the initiation of the ischemic event. As is apparent to those skilled in the art, the compounds will not correct any tissue damage that has already occurred as the result of reperfusion. As used in this application, the term "treat" refers to the ability of the compounds to prevent further damage, delay the rate at which any further damage occurs, or decrease the amount of damage which occurs.

Oxygen free radicals also produce tissue damage in other conditions besides reperfusion of ischemic tissues. Exposure to either high pressure oxygen or oxygen enriched environments produces oxygen free radicals. Extended exposure to these environments can produce tissue damage. For example, premature infants which spend extended periods of time on respirators often suffer permanent damage to their eyes and possible blindness due to these oxygen radicals. Physical trauma in which there is excessive bleeding into nervous tissues, especially the brain and spinal cord, is another example of oxygen free radicals damaging tissues. Oxygen free radicals are also generated during thrombolysis with agents such as streptokinase, TPA, etc. Oxygen free radicals are also generated by x-rays and are associated with the damage that x-rays can cause to tissue.

The generation of free radicals by a variety of cellular processes has been demonstrated during circulatory shock, septic shock and toxic shock. Over production of such radicals may be causatory in the organ damage and mortality associated with these events. Accordingly, PBN has been shown to significantly increase survival in a number of animal models of circulatory shock (Hamburger & McCay; Circulatory Shock 29:329–334 (1989) Novelli et al. Resuscitation 18 195–205 (1989). The compounds of Formula I may also be used to treat circulatory, septic, or toxic shock.

The efficacy of the compounds of Formula I has been demonstrated in an animal model of septic shock. In this test rats were injected with endotoxin and a control survival rate was determined. Other groups of rats were pretreated with one of the compounds of Formula I at varied dosages and then administered endotoxin and the survival rates were compared. This test was conducted in the following manner. Male Sprague Dawley rats were utilized (weight 215 g–300g) in each test group. Endotoxin (30 mg/kg) was administered intraperitoneally (IP). A test compound or vehicle was administered IP 30 minutes prior to endotoxin administration. The following results were obtained:

TABLE III

SURVIVAL RATES OF ENDOTOXIN TREATED RATS
(72 HOURS AFTER EXPOSURE TO ENDOTOXIN)

| Compound | Dose (mg/kg) | Survival Rate | % Surviving |
| --- | --- | --- | --- |
| Control | — | 15/60 | 25 |
| Example I | 3 | 4/12 | 33 |
| Example I | 10 | 7/12 | 58 |
| Example I | 30 | 10/12 | 83 |
| Example V | 3 | 3/10 | 30 |
| Example V | 10 | 19/23 | 91 |
| Example VI | 10 | 2/12 | 17 |
| Example VI | 30 | 10/11 | 91 |

Oxidation of tissues is also associated with a number of chronic neurodegenerative diseases. Examples of such neurodegenerative conditions include senile dementia, Alzheimer's disease and Parkinson's disease. The administration of these compounds to a patient experiencing such a disease will either prevent further neurodegeneration or decrease the rate at which further neurodegeneration occurs.

In order to exhibit the therapeutic properties described above, the compounds need to be administered in a quantity sufficient to trap oxygen free radicals and carbon centered radicals that are generated in the area at risk of tissue damage. The dosage range at which these compounds exhibit this effect can vary widely depending upon the particular disease being treated, the severity of the patient's disease, the patient, the particular compound being administered, the route of administration, and the presence of other underlying disease states within the patient, etc. Typically the compounds exhibit their therapeutic effect at a dosage range of from about 0.1 mg/kg/day to about 300 mg/kg/day for any of the diseases or conditions listed above. Repetitive daily administration may be desirable and will vary according to the conditions outlined above.

In addition to being spin trapping agents, it has also discovered that the compounds of Formula I inhibit the secretion of Interleukin-1 (IL-1). Interleukin-1 (IL-1) is the name for a family of molecules which have multiple biological effects. The name interleukin-1 was proposed in 1979; and earlier literature reports refer to it by other names. Murphy, British Journal of Rheumatogy, 1985; 24 (suppl 1): 6–9, and Oppenheimet al, Immunology Today, vol. 2, 45–55 (1986). IL-1 is secreted by stimulated macrophages, and has several significant biological effects, such as mediation of T-lymphocyte proliferation and pyrogenic and proinflammatory effects.

IL-1 activities are summarized in the two papers above. IL-1 has been described to mediate the acute phase response in inflammation, and to have pyrogenic and proinflammatory effects. IL-1 induces connective tissue changes, and has been demonstrated to induce the release of degradative enzymes from mesenchymal cells that are present at the sites of bony erosion in inflammatory disease states, such as rheumatoid arthritis. Billingham, Brit. J. Rheumatology, 1985:24(suppl 1):25–28. Dayer, Brit. J. Rheumatology, 985:24(suppl 1):21–24. The production of acute phase proteins in the hepatocytes during the acute phase of inflammation is mediated by IL-1 and other cytokines, such as IL-6. Whicher, Brit. J. Rheumatology, 1985:24(suppl 1): 21–24.

IL-1 is also involved as a mediator in the inflammatory skin disease, psoriasis. Camp et al, J. Immunology 1986: 137: 3469–3474, and Ristow, Proc. Natl. Acad. Sci. USA 1987: 84: 1940–1944. It is cytotoxic for insulin producing beta cells in the pancreas, and is thus a causative factor in the development of some forms of diabetes mellitus. Bendtzen et al., Science 1986: 232: 1545–1547 and Marx, Science 1988: 239: 257–258. IL-1 also appears to be involved in the development of atherosclerotic lesions or atherosclerotic plaque. Marx, Science 1988: 239: 257–258. IL-1 stimulates growth and proliferation of vascular smooth muscle cells, an effect which is greater in the absence or suppression of endogenous prostaglandins, which could lead to thickening of vascular walls, such as occurs in athersclerosis. Libby et al. Fed. Proc. Mar. 1, 1987: Vol. 46, no. 3: 975, Abstract 3837.

Since the compounds inhibit the secretion of IL-1 they can be utilized in the treatment of a number of disease states. These include arthritis, psoriasis, athersclerosis, and diabetes. The compounds ability to inhibit the secretion of IL-1 can be demonstrated by in-vitro and in-vivo assays known in the art. One such in-vitro assay is based upon the fact that when human macrophages are exposed to endotoxin, the macrophages secrete IL-1.

The in-vitro studies of IL-1 production was facilitated by a specific property of macrophages, i.e. attachment to non-self, e.g. plastic surface. In this assay, human peripheral blood monocyte-derived macrophages were enriched by plastic adherence. Two million of these macrophages were stimulated with 20 nanograms of endotoxin for 24 hours. Culture supernatants were then collected and the levels of IL-1 were assayed by enzyme-linked immuno-sorbent assay (ELISA). The same assay was repeated except that it was done in the presence of the test compound. The assay was repeated until an $IC_{50}$ was calculated. The following results were obtained.

TABLE IV

INHIBITION OF INTERLEUKIN-1
RELEASE BY HUMAN MACROPHAGES

| Compound | $IC_{50}$ |
| --- | --- |
| Example I | 330 uM |
| Example VI | 100 uM |
| Example V | 200 uM |

The compounds ability to inhibit the secretion of IL-1 can also be demonstrated by the following in-vivo assay which is based upon the fact that administering endotoxin to mice results in a significant rise in blood levels of IL-1 in these animals. Normal 7 week old male Charles-Dawley mice were utilized in the assay. The mice were injected with vehicle and a baseline blood level of IL-1 was established by an IL-1 specific ELISA ninety (90) minutes after administration. The animals were then administered both endotoxin and vehicle and a blood level of IL-1 was determined. Finally the animals were administered endotoxin and the test compound and the effect upon IL-1 blood levels was determined. The following results were obtained.

TABLE V

Blood Levels of Interleukin-1 in mice

| Test Compound | Endotoxin | IL-1 (picrogram/ml-serum) |
| --- | --- | --- |
| Vehicle | no | 29.2 |
| none | yes | 58.3 |
| Example 1 | yes | 6.4 |
| Example VI | yes | 10.2 |
| Example V | yes | 4.7 |

Since the compound inhibits the release of IL-1, they can be administered to treat arthritis, psoriasis, diabetes, and to prevent atherosclerosis. In order to exhibit the therapeutic properties described above, the compounds need to be administered in a quantity sufficient to inhibit the secretion of Interleukin-1. This anti-interleukin amount can vary depending upon the particular disease being treated, the severity of the patient's disease, the patient, the particular compound being administered, the route of administration, and the presence of other underlying disease states within the patient, etc. Typically the compounds exhibit their effect at a dosage range of from about 10 mg/kg/day to about 100 mg/kg/day for any of the diseases or conditions listed above. Repetitive daily administration may be desirable and will vary according to the conditions outlined above.

The compounds of the present invention may be administered by a variety of routes. They are effective if administered orally. The compounds may also be administered parenterally (i.e. subcutaneously, intravenously, intramuscularly, intraperitoneally, or intrathecally).

Pharmaceutical compositions can be manufactured utilizing techniques known in the art. Typically a protective amount of the compound will be admixed with a pharmaceutically acceptable carrier.

For oral administration, the compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations.

In another embodiment, the compounds of Formula I can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the active ingredient in an aqueous or non-aqueous pharmaceutically acceptable solvent which may also contain suspending agents, sweetening agents, flavoring agents, and preservative agents as are known in the art.

For parenteral administration the compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, buffers, etc., as are known in the art. When the compounds are being administered intrathecally, they may also be dissolved in cerebrospinal fluid as is known in the art.

The compounds of this invention can also be administered topically. This can be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety.

Some suitable transdermal devices are described in U.S. Pat. Nos. 3,742,951, 3,797,494, 3,996,934, and 4,031,894. These devices generally contain a backing member which defines one of its face surfaces, an active agent permeable adhesive layer defining the other face surface and at least one reservoir containing the active agent interposed between the face surfaces. Alternatively, the active agent may be contained in a plurality of microcapsules distributed throughout the permeable adhesive layer. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

In another device for transdermally administering the compounds in accordance with the present invention, the pharmaceutically active compound is contained in a matrix from which it is delivered in the desired gradual, constant and controlled rate. The matrix is permeable to the release of the compound through diffusion or microporous flow. The release is rate controlling. Such a system, which requires no membrane is described in U.S. Pat. No. 3,921,636. At least two types of release are possible in these systems. Release by diffusion occurs when the matrix is non-porous. The pharmaceutically effective compound dissolves in and diffuses through the matrix itself. Release by microporous flow occurs when the pharmaceutically effective compound is transported through a liquid phase in the pores of the matrix.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention As used in this application:

a) the term "patient" refers to warm blooded animals such as, for example, guinea pigs, mice, rats, gerbils, cats, rabbits, dogs, monkeys, chimpanzees, and humans;

b) the term "treat" refers to the ability of the compounds to either relieve, alleviate, or slow the progression of the patient's disease or any tissue damage associated with the disease;

c) the term "neurodegeneration" refers to a progressive death and disappearance of a population of nerve cells occurring in a manner characteristic of a particular disease state and leading to brain or other neuronal damage.

d) the term "shock" is used to refer to circulatory shock, septic shock, toxic shock, or any other condition in which oxygen derived radicals lead to inadequate pertusion of vital organs by the circulatory system.

e) the term "oxygen radical" should be construed as referring to carbon centered radicals, oxygen radicals, or any biomoleucle containing an unpaired electron in any discussion of tissue damage.

The compounds of Formula I may also be admixed with any inert carrier and utilized in laboratory assays in order to determine the concentration of the compounds within the serum, urine, etc., of the patient as is known in the art. The compounds may also be used as a research tool by forming adducts with molecular oxygen.

What is claimed is:

1. A method for the treatment of neurodegenerative diseases comprising administering to a patient in need thereof, an effective amount of a compound of the formula:

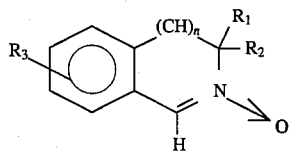

in which $R_1$ and $R_2$ are each independently represented by a $C_{1-3}$ alkyl or $R_1$ and $R_2$ together form a $C_{2-7}$ alkylene chain; n is represented by an integer from 0–2; and $R_3$ is represented by a substituent selected from the group consisting of hydrogen, halogen, $C_{1-4}$ alkyl, $C_{1-4}$ alkoxy, —$CF_3$, —$OCF_3$ and —OH.

2. A method according to claim 1 in which $R_1$ and $R_2$ together are represented by a $C_{4-7}$ alkylene chain.

3. A method according to claim 1 in which said compound is 3,4-dihydro-3,3-dimethylisoquinoline N-oxide.

4. A method according to claim 1 in which said compound is 7-chloro-3,3-dimethyl-3,4-dihydroisoquinoline-N-oxide.

5. A method according to claim 1 in which said compound is 7-fluoro-3,3-dimethyl-3,4-dihydroisoquinoline-N-oxide.

6. A method according to claim 1 in which said compound is 3,3-dimethyl-7-methoxy-3,4-dihydroisoquinoline-N-oxide.

7. A method according to claim 1 in which said compound is spiro [cyclohexane-1,3']-3,4-dihydroisoquinoline-N-oxide.

8. A method according to claim 1 in which said compound is spiro [cyclopentane-1,3']-[1H]dihydroisoquinoline-N-oxide.

9. A method according to claim 1 in which said compound is 6-chloro spiro [cyclopentane-1,3']-[1H]isoindole-N-oxide.

10. A method according to claim 1 in which said compound is 7-fluoro spiro [cyclohexane-1,3']-3,4-dihydroisoquinoline-N-oxide.

11. A method according to claim 1 in which said compound is 3,3-dimethyl-7-trifluoromethyl-3,4-dihydroisoquinoline-N-oxide.

12. A method according to claim 1 in which said compound is 3,3-dimethyl-7-hydroxy-3,4-dihydroisoquinoline-N-oxide.

13. A method according to claim 1 in which said compound is spiro [cyclopentane-1,1']-[1H]isoindole-N-oxide.

14. A method according to claim 1 in which said compound is 3,3-dimethyl-[1H]isoindole-N-oxide.

15. A method according to claim 1 in which said compound is 5-chloro-3,3-dimethyl-3,4-dihydroisoquinoline-N-oxide.

16. A method according to claim 1 in which said compound is 3,3-dimethyl-4,5-dihydro-3H-2-benazazepine-1-oxide.

17. A method according to claim 1 in which said compound is 8-chloro-3,3-dimethyl-3,4-dihydroisoquinoline-N-oxide.

18. A method according to claim 1 in which said compound is 6,8-dichloro-3,3-dimethyl-3,4-dihydroisoquinoline-N-oxide.

19. A method according to claim 1 in which said compound is 6-chloro-3,3-dimethyl-3,4-dihydroisoquinoline-N-oxide.

20. A method according to claim 1 in which said compound is spiro [cyclohexane-1,3']-7-chloro-3,4-dihydroisoquinoline-N-oxide.

21. A method according to claim 1 in which said compound is spiro [cyclohexane-1,3']-6-methoxy-3,4-dihydroisoquinoline-N-oxide.

22. A method according to claim 1 in which said compound is spiro [cyclohexane-1,3']-8-methoxy-3,4-dihydroisoquinoline-N-oxide.

23. A method according to claim 1 in which said compound is 3,3-dimethyl-6,7-dimethoxy-3,4-dihydroisoquinoline-N-oxide.

24. A method according to claim 1 in which said compound is 3,3-dimethyl-6-methoxy-3,4-dihydroisoquinoline-N-oxide.

25. A method according to claim 1 in which said compound is 3,3-dimethyl-8-methoxy-3,4-dihydroisoquinoline.

* * * * *